United States Patent [19]
Osborne et al.

[11] Patent Number: 5,776,430
[45] Date of Patent: Jul. 7, 1998

[54] TOPICAL ANTIMICROBIAL CLEANSER CONTAINING CHLORHEXIDINE GLUCONATE AND ALCOHOL

[75] Inventors: David W. Osborne, The Woodlands, Tex.; Fred Kirchner, St. Charles, Mo.

[73] Assignee: Calgon Vestal, Inc., Mentor, Ohio

[21] Appl. No.: 628,748

[22] PCT Filed: Nov. 1, 1994

[86] PCT No.: PCT/US94/12549

§ 371 Date: Aug. 20, 1996

§ 102(e) Date: Aug. 20, 1996

[87] PCT Pub. No.: WO95/12395

PCT Pub. Date: May 11, 1995

[51] Int. Cl.$^6$ .......................... A61K 9/00; A61K 31/155
[52] U.S. Cl. ................................. 424/43; 514/635

[58] Field of Search ................. 424/43; 514/635

[56] References Cited

U.S. PATENT DOCUMENTS 4,915,934  4/1990  Tomlinson .................. 424/45

*Primary Examiner*—Kimberly R. Jordan
*Attorney, Agent, or Firm*—Fay, Sharpe, Beall, Fagan, Minnich & McKee

[57] ABSTRACT

The combination of chlorhexidine gluconate (CHG), SDA-3 ethyl alcohol and cetyl lactate has produced a highly effective topical antimicrobial cleanser having immediate, persistant and residual bactericidal activity. The invention also relates to a low temperature manufacturing process for producing chlorhexidine salts in alcohol based formulations.

17 Claims, No Drawings

TOPICAL ANTIMICROBIAL CLEANSER CONTAINING CHLORHEXIDINE GLUCONATE AND ALCOHOL

This application is a 371 of PCT/US94/12549, filed Nov. 1, 1994.

BACKGROUND OF THE INVENTION

Chlorhexidine (Rose, Swain, *J. Chem. Soc.* 1956, 4422, U.S. Pat. No. 2,684,924) and its salts, including the gluconate salt (CHG), is well known as a water soluble topical antimicrobial (G. E. Davies et al. *Brit. J. Pharmacol.* 9, 192 (1954) and D. M. Foulkes, *J. Peridont. Res.* 8, Suppl. 12., 55–60 (1973)). Numerous compositions containing CHG as an active ingredient to fight microbial infection after surgery or during wound healing are known. Chlorhexidine and its salts are effective against a wide range of Gram-positive and Gram-negative bacteria. It is also effective against Proteus and against some fungi and viruses. CHG is currently marketed in compositions sold and directly applied at a 4% concentration level e.g., HIBICLENS™ (commercially available from Stuart Pharmaceuticals),to achieve an antimicrobial effect.

The combination of an alcohol and CHG is known. For example, the combination of CHG and denatured alcohol containing the denaturant brucine sulfate is known as a composition useful in surgical scrub applications. The combination of a bisbiguanide such as CHG, and an alcohol such as isopropanol or ethanol is also known. See U.S. Pat. Nos. 5,164,107 or 5,089,205. Four percent of isopropanol was added to stock solutions of CHG in the '107 disclosure to prevent the contamination of the stock solution with species of Pseudomonas.

Solutions of 0.5% CHG with 70% isopropanol, and 1.0% CHG with 50% ethanol, were described as skin-disinfectant (see Beeuwkes et al., *Acta Therapeutica* 11 (1985) pp. 445–451, and Beeuwkes et al., *Journal of Hospital Infection* 8 (1986) pp. 200–202).

The present invention is a cleanser system of CHG and a denatured alcohol, which is highly effective as an antimicrobial surgical scrub or hand wash composition and is more effective than the prior art compositions.

SUMMARY OF THE INVENTION

The present invention is directed to a composition comprising a cleanser system of between about 0.65 and 0.85 wt. % antimicrobial agent chlorhexidine or a pharmaceutically acceptable salt thereof and between about 50 and 60 wt. % denatured alcohol. The denatured alcohol is Specially Denatured Alcohol SDA 3-C, which is a commercial, nonbeverage grade denatured alcohol defined by the Alcohol and Tobacco Tax Division of the Internal Revenue Service as ethanol with a 5% isopropanol denaturant (i.e., 95% ethanol/5% isopropanol). This system has significantly improved and faster-acting antimicrobial properties and may be used in surgical scrubs and in wound dressings. Additional inert or antimicrobial active ingredients may be added to the system. The system is applied, as a foaming scrub or aerosol product, to a patient or organism in order to achieve an antimicrobial affect.

The present invention is also directed to a process for making the CHG/denatured alcohol system which avoids the need for high-temperature processing. Production according to this process obviates the need for explosion-proof facilities which would otherwise be required because of the high alcohol content of the system.

Preferably, the antimicrobial agent is chlorhexidine gluconate, and the system may further comprise a corrosion inhibitor, a pH modifier, an emollient, and a foaming agent.

Preferably, the denatured ethanol is anhydrous denatured ethanol SDA 3-C, the corrosion inhibitor is selected from the group consisting of benzoate salt, a nitrite salt, and a borate salt, the pH modifier is selected from the group consisting of sodium sesquicarbonate, a carbonate salt, a citrate salt, and an acetate, the emollient is selected from the group consisting of cetyl lactate and stearyl lactate, and the foaming agent is selected from the group consisting of an Emulsifying Wax NF, and a blend of stearyl alcohol and cetyl alcohol.

More preferably, the chlorhexidine gluconate is present in a relative weight range of between 0.65 and 0.85 wt. %, anhydrous ethanol SDA 3-C is present in a relative weight range of between 50 and 60 wt. %, the corrosion inhibitor is sodium benzoate present in a relative weight range of between 0.01 and 0.8%, the pH modifier is sodium sesquicarbonate present in a relative weight range of between 0.01 and 0.5%, the emollient is cetyl lactate present in a relative weight range of between 0.01 and 1%, the Emulsifying Wax is Polawax A-31 present in a relative weight range of between 0.2 and 5%, and the remainder is water.

In even more prefered formulations, the amount of denatured ethanol SDA-3C is between about 50 and 60 wt. %, the amount of Polawax A-3 1 is between about 1–2 wt. %, the amount of cetyl lactate is between about 0.1–0.3 wt. %, the amount of sodium benzoate is between about 0.1–0.2 wt. %, the amount of sodium sesquicarbonate is between about 0.05–0.1 wt. %, the amount of CHG is between about 0.7–0.85 wt. %, and the remainder is water. Formulations where the amount of water represents the remainder of the formulation are shown to contain an amount of water identified as "QS," the quantity sufficient to identify 100% of the composition.

Most preferably, the antimicrobial formulation has the following relative weight percentages: about 56.72% denatured ethanol SDA 3-C, about 1.52% Polawax A-31, about 0.24% cetyl lactate, about 0.16% sodium benzoate, about 0.08% sodium sesquicarbonate, about 21.28% water, and about 0.8 wt. % CHG.

Antimicrobial formulation of the invention administered via aerosol spray further comprise a propellant.

The formulations prevent organism growth and multiplication on a mammalian skin surface and are therefore useful disinfectants for disinfecting such surfaces. The formulations can be topically administered, via foam rub-in or aerosol spray.

The invention also includes a process for producing a formulation of the invention in an explosion-proof environment, wherein the formulation comprises an amount of denatured ethanol SDA-3C between about 50 and 60 wt. %, an amount of Polawax A-31 between about 1–2 wt. %, an amount of cetyl lactate between about 0.1– 0.3 wt. %, an amount of sodium benzoate between about 0.1–0.2 wt. %, an amount of sodium sesquicarbonate between about 0.05–0.1 wt. %, an amount of CHG between about 0.7–0.85 wt. %, and the remainder water, comprising the steps of adding purified water to a mix tank, agitating the water, adding sodium benzoate to the mix tank during agitation, adding sodium sesquicarbonate to the mix tank during agitation, heating the mix to 105°–110° F., maintaining the temperature at 105°–110° F. while adding cetyl lactate, Polawax A-31 and SDA 3-C ethanol to the mix tank, mixing until homogenous, maintaining a temperature at 105°–110° F. while adding a 20% aqueous CHG solution to the mix tank, mixing for at least 15 minutes or until the mix is homogenous, and maintaining the temperature at 100°–110° F. until filling is completed.

The invention also includes a low temperature process for producing a formulation of the invention in a non-explosion proof environment comprising the steps of:

A) adding a sufficient amount of denatured ethanol SDA 3-C to a mix tank, agitating the denatured ethanol SDA 3-C, adding a sufficient amount of Polawax A-31 to the mix tank during agitation, adding a sufficient amount of cetyl lactate to the mix tank during agitation, mixing for at least 30 minutes or until the Polawax A-31 and the cetyl lactate are completely dissolved, adding a sufficient amount of sodium benzoate to the mix tank, adding a sufficient amount of sodium sesquicarbonate to the mix tank, slowly adding a sufficient amount of water to the mix tank, and mixing for at least 30 minutes, to form Phase A comprising the following components:

| | |
|---|---|
| denatured alcohol SDA 3-C | about 65–75% |
| Polawax A-31 | about 1.5–2.5% |
| cetyl lactate | about 0.2–0.4% |
| sodium benzoate | about 0.1–0.3% |
| sodium sesquicarbonate | about 0.05–0.15% |
| water (distilled) | QS; |

B) adding a sufficient amount of water to a mix tank, agitating the water, adding a sufficient amount of 20% CHG solution to the mix tank during agitation, and mixing for at least 30 minutes, to form Phase B comprising the following components:

| | |
|---|---|
| 20 wt. % solution CHG | about 15.0–25.0% |
| water (distilled) | QS; | and

C) combining Phase A and Phase B in an aerosol container in a weight ratio of about 80:20, and introducing a propellant blend into the aerosol container.

Preferably, in the process, Phase A comprises

| | |
|---|---|
| denatured alcohol SDA 3-C | about 70.9% |
| Polawax A-31 | about 1.9% |
| cetyl lactate | about 0.3% |
| sodium benzoate | about 0.2% |
| sodium sesquicarbonate | about 0.1% |
| water (distilled) | QS; | and Phase B comprises

| | |
|---|---|
| 20 wt. % solution CHG | about 20.0% |
| water (distilled) | QS. |

DETAILED DESCRIPTION OF THE INVENTION

This invention relates to a composition comprising chlorhexidine gluconate (CHG) and denatured alcohol SDA 3-C, which is useful as an effective topical antimicrobial cleanser.

The system of CHG and denatured alcohol SDA 3-C and additional inert reagents may readily be prepared by combining various selected reagents. For instance, distilled water may be added to a mixing vessel of any suitable size depending upon the target quantity desired with subsequent addition of sodium benzoate, sodium sesquicarbonate, cetyl lactate, an Emulsifying Wax (e.g. Polawax A-31), SDA 3-C (e.g. SDA 3-C anhydrous), and an aqueous solution, e.g. 20% wt. solution, of CHG.

The sodium sesquicarbonate provides modest corrosion inhibition but primarily adjusts the pH so that the primary corrosion inhibitor, sodium benzoate, functions optimally. Corrosion inhibition is required for tin-plated steel cans and certain cup and valve contact surfaces. Corrosion inhibitors are not necessary to protect aluminum can surfaces. Alternate excipients for sodium sesquicarbonate would be any ionizable substance that would optimize the pH of the system, i.e. approximately pH 9 for the above listed components. Alternate corrosion inhibitors would include other benzoates, nitrites, or borates.

Cetyl lactate is included in the formulation as an emollient and also reduces the tacky feel characteristics of CHG. Polawax A3 1 is the foaming agent. Similar foaming performance would be anticipated by use of any Emulsifying Wax NF (National Formulary), combination of stearyl alcohol and cetyl alcohol, or other wax combinations.

The propellant blend provides pressure for dispersing the product from the can and also partially dissolves into the formulation resulting in complete dissolution of the waxes. Any blend of propellants that provides the concentrate as a solution could be readily substituted for the Isobutane/Propane A-40 and 1,1-Difluoroethane P-152a blend used in the tested formulation.

The relative percentages of each of the reagents may vary depending upon the desired strength of the target formulation or solution. The order of addition of the reagents may be important depending on which reagents are added or necessary for the target mixture. For example, if an initial formulation is prepared without a CHG solution, and Polawax A-31 and cetyl lactate are used, the latter components must be dissolved in ethanol prior to addition of water in order to prevent precipitation of the Polawax and the cetyl lactate and to quicken the dissolution process. After addition of the alcohol blend and the CHG solution, the concentrate may be heated to 100°–110° F. until filling is completed. The claimed formulation can be prepared in explosion-proof facilities or may be prepared by a two-phase process that obviates the need for high-temperature processing and explosion-proof facilities.

A concentrate of the claimed formulation may contain insoluble material such as wax when cooled below 100° F. Because the flash point of a liquid CHG-alcohol formulation is about 75° F., high temperature (100°–110° F.) processing and filling can only be completed in explosion proof facilities. Room temperature processing and filling can be acheived by a two-phase process without precipitation of the waxes. Room temperature processing does not require explosion proof facilities.

If explosion proof facilities are used for the manufacture and filling processes, purified water USP (United States Pharmacopoeia), sodium benzoate NF, and sodium sesquicarbonate CTFA (Cosmetics and Toiletries Fragrance Association) are added to a stainless or glass lined mixing tank and heated to 100°–110° F. with agitation. Cetyl lactate CTFA, Polawax A-31 NF and SDA 3-C ethanol anhydrous are then added with mixing while maintaining the temperature at 100°–110° F. Upon obtaining a homogenous solution, the CHG solution BP (British Pharmacopoeia) is added and mixed adequately to obtain a homogenous solution. The completed liquid formulation is maintained at 100°–110° F. during filling with precautions taken to prevent ethanol evaporation.

If either the manufacturing tank or the filling line are not explosion proof, a two part filling operation must be completed. In a tank capable of holding and adequately mixing about 80% of the final liquid concentrate batch, SDA 3-C ethanol anhydrous must be added first, followed by Polawax A-31 NF and cetyl lactate, mixing until the waxes have completely dissolved. Water is then added, followed by sodium benzoate NF and sodium sesquicarbonate CTFA. Adequate mixing must be maintained to homogeneously disperse the fine needle crystals characteristic of sodium sesquicarbonate. In the following examples, this liquid concentrate is labeled "Part A."

"Part B" of the two-phase process requires the use of a manufacturing tank capable of holding and adequately mixing about 20% of the final liquid formulation batch. To this tank, the appropriate weight of active CHG solution, e.g. a 20 wt. % aqueous CHG solution, is added.

Parts A and B are maintained at ambient conditions during filling into an aerosol can. Part A is added to 80% of the liquid formulation target fill weight. Fill weights for both Part A and Part B are checked until five consecutive cans are within ±5% of the target weight without adjustment of fill. Fill weights for both Part A and B are then checked and recorded throughout the remainder of the filling process.

The propellants which may be used in the present invention in order to prepare an aerosol can include any blend of propellants that provide the concentrate as a solution such as a Isobutane/Propane A-40 and 1,1-Difluoroethane P-152a blend. The propellants are pre-blended, with the mix ratio being verified by gas chromatographic analysis. The amount of propellant required to properly disperse the contained formulation can readily be determined by persons skilled in the art. Gas samples are taken at the gassing head after flushing all lines with propellant, and the sample may be analyzed by gas chromatography to verify the propellant identity. Cans are under-the-cup filled and the propellant fill weight is checked and recorded throughout the entire filling process. Crimp depth and diameter are monitored. Each can then passes submerged through a hot tank that is maintained at a temperature which provides an internal can pressure of 130 psi or greater. Submerged bubbling cans are readily identified as leaking and defective. Cans are then air dried and ink jet imprinted with Lot number. Actuators are properly placed and the cans are overcapped. The cleanser and propellant form a single phase solution at room temperature, as determined using aerosol compatibility vessels.

The CHG and denatured alcohol SDA 3-C system produces a surprisingly improved topical antimicrobial action as compared to previously known antimicrobial surface cleansers. The composition has immediate, persistent and residual bactericidal activity. The claimed formulation causes significantly greater microbial population reductions at various stages in the antimicrobial process, including the time period immediately after scrub, 3 hours post-scrub and six hours post-scrub, than products such as a rub-in alcohol based formulation containing no CHG, or the commercially available 4% CHG surgical handscrub HIBICLENS™ (commercially available from Stuart Pharmaceuticals) (Table III).

For example, after five days of use and six hours of post-scrub, a rub-in CHG and SDA 3-C alcohol foam formulation at a CHG concentration range of 0.67%–0.83% will cause a one $\log_{10}$ greater reduction in the microbial population than a 4% CHG solution scrubbed onto the skin with a brush.

EXAMPLE 1

Two-Phase Process For Preparing an Ambient CHG-Alcohol Blend

Part A and Part B were prepared as follows.

| Part A | |
|---|---|
| denatured alcohol SDA 3-C | 70.9% |
| Polawax A-31 | 1.9% |
| cetyl lactate | 0.3% |
| sodium benzoate | 0.2% |
| sodium sesquicarbonate | 0.1% |
| water (distilled) | 26.6% |

Clean and sanitized stainless steel equipment was used in the production of Part A. The fill temperature of the product was 70°–78° F. and constant agitation was maintained during the filling process. 713 pounds of denatured alcohol SDA 3-C was added to the mix tank. Agitation was started and 18.9 pounds Polawax A-31 and 3.1 pounds of cetyl lactate were added to the mix tank. The mixture was agitated until the Polawax A-31 and the cetyl lactate were completely dissolved and was mixed for a minimum of thirty (30) minutes. After this period, 2.50 pounds of sodium benzoate was added to the agitating mixture followed by 1 pound of sodium sesquicarbonate. Agitation was continued while 267.5 pounds of distilled water was added to the mix tank. The mixture was then stirred for at least an additional thirty (30) minutes. This produced a total of 1006 pounds of Part A.

In order to properly dissolve the Polawax and the cetyl lactate, the order of addition of the reagents is critical. The Polawax A-31 and cetyl lactate must be dissolved in the ethanol before the water is added. After addition of water to the alcohol/wax solution, sodium benzoate rapidly dissolves. Adequate mixing must be maintained to homogeneously disperse sodium sesquicarbonate during filling.

| Part B | |
|---|---|
| 20 wt. % solution CHG | 20.0% |
| water (distilled) | 80.0% |

Clean and sanitized stainless steel equipment was used in the production of a Phase B formulation. The fill temperature of the product was 70°–78° F. Constant agitation was maintained during the filling process in the fifty-five gallon batch tank. 243.75 pounds of distilled water (pH 6.15 with <0.5 ppm NaCl) was added to the mix tank. 56.25 pounds of a 20% CHG solution was added to the tank with agitation and stirred for a minimum of thirty (30) minutes. This produced a total of 300 pounds of Part B.

Filling

Parts A and B were maintained at ambient conditions during filling into an aerosol can. Part A was added to 80% of the liquid formulation target fill weight. Fill weights for both Part A and Part B were checked initially for each can until five consecutive cans were within ±5% of the target weight without adjustment of fill. Fill weights for both Part A and B were then checked and recorded for no less than each thirty (30) cans for the remainder of the filling process.

The propellant, one third Isobutane/Propane A-10 and two-thirds 1,1 Difluoroethane P-152a, was pre-blended with the mix ratio being verified by gas chromatographic analysis. The amount of propellant required to properly disperse the contained formulation can readily be determined by persons skilled in the art. Gas samples were taken at the gassing head after flushing all lines with propellant, and the sample was analyzed by gas chromatography to verify the propellant identity. Cans were under-the-cup filled and the propellant fill weight was checked and recorded for each thirtieth can for the entire filling process. Crimp depth and diameter were monitored. Each can was then passed submerged through a hot tank maintained at a temperature to assure that each can experienced an internal pressure of 130 psi or greater. Since leaking cans are readily identified by bubbling while submerged, 100% leak testing was completed. The cans were then air dried and ink jet imprinted with Lot number. Actuators were properly placed and the cans were overcapped. The CHG/denatured alcohol SDA 3-C system with propellant forms a single phase solution at room temperature as determined using aerosol compatibility vessels.

Phase A and Phase B were combined in an aerosol container in a weight ratio of about 80:20. For example, a 211 mm×713 mm tin-plate aerosol package is filled with 392.2+/−3 grams of Phase A and 98.0+/−1 gram of Phase B prior to gassing with 25.8+/−2 grams of the propellant blend. A 53 mm×165 mm aluminum aerosol package is filled with 196.0+/−1 gram of Phase A and 49.0+/−1 gram of Phase B prior to gassing with 12.9+/−1 gram of the propellant blend. A 45 mm×140 mm aluminum aerosol package is filled with 118.6+/−1 gram of Phase A and 29.6+/−1 gram of Phase B prior to gassing with 7.8+/−1 gram of the propellant blend. A constant ratio of 80:20 Phase A:Phase B is required for a 0.75% CHG label claim.

Following the combination of Phase A with Phase B, and introduction of propellant into the aerosol containing, the amount of CHG present in the container was about 0.75 wt. %. Following activation of the aerosol container for application to the target surface, propellant dissipates, and the concentration of CHG contacting the target surface was about 0.79 wt. %.

EXAMPLE 2

Component Weights per 100 Grams Concentrate

Specific weight amount for the procedure described in Example 1 are shown below:

| Component | wt/100 g product |
| --- | --- |
| Part A | |
| denatured alcohol SDA 3-C | 56.7 g |
| Polawax A-31 | 1.5 g |
| cetyl lactate | 0.25 g |
| sodium benzoate | 0.2 g |
| sodium sesquicarbonate | 0.1 g |
| water USP | 21.25 g |
| Part B | |
| 20 wt. % solution CHG | 3.95 g |
| water USP | 16.05 g |

80 grams of Part A was added to 20 grams of Part B to produce the liquid concentrate prior to addition of a propellant. The filled product is referred to as Septisol 0.75% CHG Foam.

EXAMPLE 3

When explosion proof facilities were used for the manufacture and filling processes, purified water USP, sodium benzoate NF, and sodium sesquicarbonate CTFA, in the quantities shown in Example 1, were added to a stainless or glass lined mixing tank and heated to 100°–110° F. with agitation. The cetyl lactate CTFA, Polawax A-31 NF and the SDA 3-C ethanol anhydrous in the quantities listed above were then added with mixing while maintaining the temperature at 100°–110° F. Upon obtaining a homogenous solution, the CHG solution BP was added and mixed adequately to obtain a homogenous solution. The completed liquid formulation was maintained at 100°–110° F. during filling with all possible precautions being taken to prevent ethanol evaporation.

The formulation was filled with propellant in an aerosol container according to the procedure described in Example 1. The filled product is referred to as Septisol 0.75% CHG Foam.

EXAMPLE 4

Evaluation

Septisol 0.75% CHG Foam, Septisol vehicle (Septisol 0.75% CHG Foam formulation excluding active CHG) and HIBICLENS™ 4% CHG were topically applied and evaluated for immediate, persistent (three hours after application), and residual (six hours after application) effects. Eighteen subjects per product were evaluated using a glove juice sampling procedure detailed below. Fourteen days prior to the test portion of the study constituted the pre-test period. During this time, subjects avoided the use of medicated soaps, lotions, deodorants and shampoos and avoided skin contact with solvents, detergents, acids and bases. This regimen allowed for the stabilization of the normal microbial populations residing on the hands.

The week following the pre-test period was designated the baseline period. Baseline determinations were taken on days one, three, and five of that week. The average $\log_{10}$ baseline value was 6.495, with a standard deviation of 0.730 (N=108). Subjects were randomly assigned to one of three study groups and sampled. Following the prescribed wash and rinse, excess water was shaken from the hands and powder-free sterile gloves were donned. At the designated sampling time, 75 mls of sterile 0.1M phosphate buffered (pH 7.8–7.9) aqueous solution containing 0.1% Triton X-100 was instilled into the glove. The wrist was secured and an attendant massaged the hand through the glove in a standardized manner for 60 seconds. Aliquots of the glove juice were removed and serially diluted in Trypticase Soy Broth (TSB) containing 1.0% Tween 80 and 0.3% Lecithin as product neutralizers.

Solidified plates were incubated at 30°–35° C. for up to 48 hours. Those plates providing colony counts between 25 and 250 were preferentially used in this study. If no plates provided counts in the 25–250 range, the plates closest to that range were counted and used in determining the number of viable microorganisms. Summary results of the test week are given in Table I.

The directions for using Septisol 0.75% CHG Foam and Septisol Vehicle were as follows. A palm full (5 grams) of Septisol 0.75% CHG Foam, supplied by an attendant, is dispensed into one hand. It is spread on both hands and forearms and rubbed into the skin until dry (approximately 1 to 1.5 minutes). A smaller amount (2.5 grams), supplied by an attendant, is then dispensed into one hand, spread over both hands and forearms and rubbed into the skin until dry (approximately 0.5 minutes.)

The directions for using HIBICLENS™ 4% CHG Solution with Sterile EZ Scrub Brush (Stuart Pharmaceuticals) included the following six minute scrub procedure:

1. Wet hands and forearms with warm water. Use nail cleaner.

2. Apply 5 ml HIBICLENS™ 4% CHG Solution on sponge side. Work up lather.
3. Scrub for 3 minutes as follows. With the brush side of the product, scrub nails, cuticles, and interdigital spaces. Scrub hands and forearms with sponge side.
4. Rinse thoroughly with warm water.
5. Repeat scrub for 3 minutes using sponge side only.
6. Rinse thoroughly.
7. Dry thoroughly with sterile towel supplied by an attendant.

TABLE 1

Microbial Population Reduction

| Day | Immediately After Scrub | | | 3 Hours After Scrub | | | 6 Hours After Scrub | | |
|---|---|---|---|---|---|---|---|---|---|
| | $\bar{x}$ | s | r | $\bar{x}$ | s | r | $\bar{x}$ | s | r |
| Septisol 0.75% CHG Foam | | | | | | | | | |
| 1 | 3.00 | 0.99 | 3.49 | 4.48 | 1.06 | 2.01 | 5.06 | 0.98 | 1.43 |
| 2 | 2.79 | 1.03 | 3.70 | 4.09 | 0.81 | 2.40 | 4.28 | 0.97 | 2.21 |
| 5 | 2.70 | 0.57 | 3.79 | 3.22 | 0.71 | 3.27 | 2.89 | 1.54 | 3.60 |
| Septisol Vehicle (no CHG) | | | | | | | | | |
| 1 | 4.85 | 1.00 | 1.64 | 6.41 | 0.33 | 0.08 | 6.37 | 0.49 | 0.12 |
| 2 | 4.15 | 1.00 | 2.34 | 6.07 | 0.39 | 0.42 | 6.18 | 0.86 | 0.31 |
| 5 | 3.65 | 0.79 | 2.84 | 5.56 | 0.69 | 0.63 | 5.75 | 0.69 | 0.74 |
| HIBICLENS™ 4% CHG Solution | | | | | | | | | |
| 1 | 5.11 | 0.76 | 1.38 | 5.58 | 0.53 | 0.91 | 5.73 | 0.63 | 0.76 |
| 2 | 4.20 | 0.84 | 2.29 | 4.76 | 1.47 | 1.73 | 5.02 | 0.60 | 1.47 |
| 5 | 2.25 | 1.65 | 4.24 | 4.00 | 1.46 | 2.49 | 3.94 | 1.09 | 2.55 |

This study concludes that Septisol 0.75% CHG Foam is clearly better than HIBICLENS™ 4% CHG Solution applied with a scrub brush in reducing skin microflora immediately after use on days 1 and 2, i.e. immediate activity. Likewise, Septisol 0.75% Foam is more effective than HIBICLENS™ 4% CHG Solution applied with a scrub brush in reducing skin microflora three hours (persistent activity) and six hours (residual activity) after use on days 1, 2, and 5.

What is claimed is:

1. An antimicrobial foam formulation comprising:
   (a) between about 0.65 and 0.85 wt. % chlorhexidine or a pharmaceutically acceptable salt thereof;
   (b) between about 0.1 and 0.4 wt. % cetyl lactate or a pharmaceutically acceptable salt thereof;
   (c) between about 50 and 60 wt. % ethyl alcohol;
   (d) between about 1.0 and 2.0 wt. % emulsifying wax NF; and,
   (e) an aerosol propellant.

2. The antimicrobial foam formulation as set forth in claim 1 further comprising:
   0.05–0.1 wt. % sodium sesquicarbonate; and,
   0.1–2.0 wt. % sodium benzoate.

3. A method for manufacturing the antimicrobial formulation as set forth in claim 2 comprising:
   adding the sodium benzoate to purified water and agitating;
   during the agitation, adding the sodium sesquicarbonate and heating the mixture to about 105°–110° F.;
   maintaining the temperature between 105°–110° F. and adding the cetyl lactate, the emulsifying wax NF, and the ethyl alcohol;
   while maintaining the temperature at 105°–110° F., mixing while adding the chlorhexidine;
   continuing the mixing until homogeneous; and,
   filling an aerosol container with the mixture and the aerosol propellant.

4. The antimicrobial foam formulation as set forth in claim 2 wherein the ethyl alcohol is denatured with about 5% isopropanol.

5. The antimicrobial foam formulation as set forth in claim 4 wherein the chlorhexidine is present as a gluconate salt.

6. A method of preventing microorganism growth comprising administering an antimicrobial therapeutically effective amount of the formulation of claim 1 to the microorganism.

7. A method of disinfecting a mammal comprising topically administering an antimicrobial therapeutically effective amount of the formulation of claim 1.

8. An antimicrobial foam formulation for topical disinfection, the formulation comprising:
   (a) chlorhexidine gluconate;
   (b) 0.1 to 0.4 wt. % cetyl lactate as an emollient;
   (c) a slow breaking alcohol foam comprising
      (i) ethyl alcohol,
      (ii) an emulsifying wax, NF, and,
      (iii) water;
   (d) an aerosol propellant;
   (e) a corrosion inhibitor;
   (f) a pH modifier.

9. The antimicrobial formulation as set forth in claim 8 wherein the chlorhexidine gluconate is present between about 0.65–0.85 wt. %;
   the alcohol is present between 50–60 wt. %;
   the emulsifying wax is present between 1.0 and 2.0 wt. %.

10. The antimicrobial formulation as set forth in claim 9 wherein the aerosol propellant is 1,1 difluoroethane.

11. The antimicrobial formulation as set forth in claim 9 wherein the pH modifier is sodium sesquicarbonate.

12. The antimicrobial formulation as set forth in claim 11 wherein the corrosion inhibitor is sodium benzoate.

13. The formulation as set forth in claim 9 wherein the alcohol is denatured ethanol.

14. The formulation as set forth in claim 13 wherein the ethanol is denatured with 5% isopropanol.

15. A method of disinfecting hands comprising topically administering water and an antimicrobial therapeutically effective amount of the formulation as set forth in claim 8 to the hands, rubbing the hands, and rinsing with water.

16. An antimicrobial formulation for topical disinfection comprising:
   (a) between about 0.65–0.85 wt. % chlorhexidine gluconate;
   (b) between about 0.1 to 0.4 wt. % cetyl lactate as an emollient;
   (c) a slow breaking alcohol foam comprising:
      (i) between about 50–60% wt. % ethyl alcohol,
      (ii) between about 1.0–2.0 wt. % emulsifying wax, NF, and;
      (iii) water;
   (d) an aerosol propellant;
   (e) a corrosion inhibitor;
   (f) a pH modifier;
   wherein the cetyl lactate reduces a tacky feeling characteristic of chlorhexidine gluconate.

17. The antimicrobial formulation as set forth in claim 16 wherein:
   the pH modifier comprises sodium sesquicarbonate present between 0.5 and 0.1 wt. %.

* * * * *